US011446433B2

(12) United States Patent
Endo et al.

(10) Patent No.: US 11,446,433 B2
(45) Date of Patent: Sep. 20, 2022

(54) FEEDING DEVICE AND PORTABLE DISPENSING DEVICE

(71) Applicant: Seiko Instruments Inc., Chiba (JP)

(72) Inventors: Yoichi Endo, Chiba (JP); Akehiko Sato, Chiba (JP); Masami Oaku, Chiba (JP); Shinichi Asai, Yokohama (JP)

(73) Assignee: SEIKO INSTRUMENTS INC., Chiba (JP)

( * ) Notice: Subject to any disclaimer, the term of this patent is extended or adjusted under 35 U.S.C. 154(b) by 238 days.

(21) Appl. No.: 16/703,363

(22) Filed: Dec. 4, 2019

(65) Prior Publication Data

US 2020/0215262 A1 Jul. 9, 2020

(30) Foreign Application Priority Data

Jan. 8, 2019 (JP) .............................. JP2019-001085

(51) Int. Cl.
*A61M 5/145* (2006.01)
*A61M 5/142* (2006.01)
*A61M 5/315* (2006.01)

(52) U.S. Cl.
CPC ...... *A61M 5/1454* (2013.01); *A61M 5/14248* (2013.01); *A61M 5/31528* (2013.01);
(Continued)

(58) Field of Classification Search
CPC ............ A61M 5/1454; A61M 5/14248; A61M 5/31528; A61M 2205/103; A61M 2205/50; A61M 2205/8206; A61M 2005/3152
See application file for complete search history.

(56) References Cited

U.S. PATENT DOCUMENTS 7,066,909 B1 * 6/2006 Peter .................. A61M 5/14244
604/134
2005/0000711 A1 * 1/2005 Hurlstone ........... A61M 5/2046
173/19
(Continued)

FOREIGN PATENT DOCUMENTS

JP 2003-501157 A 1/2003
JP 2003-527217 A 9/2003
(Continued)

OTHER PUBLICATIONS

Office Action in Japan Application No. 2019-001085, including English translation, dated Jun. 28, 2022, _ pages.

*Primary Examiner* — James D Ponton
(74) *Attorney, Agent, or Firm* — Crowell & Moring LLP

(57) ABSTRACT

A feeding device according to the present invention includes a tubular body which has an a female screw portion, a movable shaft which has a male screw portion and is movable between a start position and an end position according to a rotation of the tubular body, a final gear which is provided in the tubular body, a drive unit which has the driving gear, a power transmission mechanism which transmits a driving force from the driving gear to the final gear via a plurality of intermediate gears, and a biasing mechanism which is configured to apply a biasing force to the movable shaft. At least one of the plurality of intermediate gears is a two-stage gear. The biasing mechanism is configured to apply the biasing force from the end position toward the start position and presses the male screw portion against the female screw portion to the start position side.

10 Claims, 10 Drawing Sheets

(52) U.S. Cl.
CPC ... *A61M 2205/103* (2013.01); *A61M 2205/50* (2013.01); *A61M 2205/8206* (2013.01)

(56) References Cited

U.S. PATENT DOCUMENTS

| | | | |
|---|---|---|---|
| 2010/0160861 A1* | 6/2010 | Causey, III | A61M 5/1456 604/131 |
| 2012/0172817 A1* | 7/2012 | Bruggemann | A61M 5/14566 604/218 |
| 2014/0148785 A1* | 5/2014 | Moberg | A61M 5/14244 604/506 |
| 2016/0058949 A1* | 3/2016 | Bayer | A61M 5/315 604/207 |
| 2019/0015585 A1* | 1/2019 | Smith | A61M 5/14248 |

FOREIGN PATENT DOCUMENTS

| | | |
|---|---|---|
| JP | 2006-195179 A | 7/2006 |
| JP | 2007-528260 A | 10/2007 |
| JP | 2010-509984 A | 4/2010 |
| JP | 2010-538799 A | 12/2010 |
| JP | 2014-507223 A | 3/2014 |
| WO | WO 00/74752 A1 | 12/2000 |
| WO | WO 01/70307 A1 | 9/2001 |
| WO | WO 2005/094921 A1 | 10/2005 |
| WO | WO 2008/063429 A2 | 5/2008 |
| WO | WO 2009/039214 A2 | 3/2009 |
| WO | WO 2012/110474 A1 | 8/2012 |

\* cited by examiner

FEEDING DEVICE AND PORTABLE DISPENSING DEVICE

RELATED APPLICATIONS

This application claims priority to Japanese Patent Application No. 2019-001085 filed on Jan. 8, 2019, the entire content of which is incorporated herein by reference.

BACKGROUND OF THE INVENTION

1. Field of the Invention

The present invention relates to a feeding device and a portable dispensing device.

2. Description of the Related Art

In the related art, for example, as described in Published Japanese Translation Nos. 2010-509984 and 2007-528260 of the PCT International Publication, as a device for feeding a liquid, a liquid feeding device is known, which feds a liquid filling a reservoir into a human body by moving a plunger by driving a gear.

The liquid feeding device includes a drive motor having a drive shaft, a plurality of spur gears which are rotated according to a rotation of the drive shaft, a feed screw which is rotated by rotations of the plurality of spur gears, and a cylindrical slider which is configured to move in an axial direction of the feed screw according to a rotation of the feed screw. The plurality of spur gears are disposed to be arranged in parallel in a state of meshing with each other. A male screw portion is formed on an outer peripheral surface of the feed screw. A female screw portion which is screwed to the male screw portion of the feed screw is formed on an inner peripheral surface of the slider. The feed screw is attached to the spur gear which is located at a final stage among the plurality of spur gears. The slider is in pushable contact with a reservoir plunger of the reservoir filled with a liquid.

In a case where the liquid is fed using the liquid feeding device, the drive shaft is rotated by driving the drive motor. Accordingly, the feed screw can be rotated via the plurality of spur gears, and the slider can be fed and moved in the axial direction of the feed screw. Accordingly, the reservoir plunger can be pushed in using the slider, and the liquid in the reservoir can be extruded to the outside by a pushing-in amount of the reservoir plunger. As a result, the extruded liquid can be fed into a human body. Particularly, it is possible to adjust a rotational speed of the feed screw, which is rotated according to the rotation of the drive motor, by a gear ratio of the plurality of spur gears, and thus, it is possible to adjust an amount of movement of the slider. In addition, for example, in Published Japanese Translation Nos. 2003-527217 and 2003-501157 of the PCT International Publication, a liquid feeding device similarly configured to the above-described liquid feeding device is disclosed.

SUMMARY OUT THE INVENTION

In a liquid feeding device of the related art, in order to extrude a desired amount of liquid from a reservoir, it is necessary to accurately move a slider. However, in the liquid feeding device of the related art, a drive force of a drive motor is transmitted to a slider via fitting (meshing) between a male screw portion of a feed screw and a female screw portion of a slider finally. However, in general, backlash (gap) is generated in a fitting portion between the male screw portion and the female screw portion, and thus, rattling is easily generated in the slider due to the backlash. Accordingly, it is difficult to stably and accurately move the slider, and thus, there is room for improvement.

Moreover, a plurality of spur gear are disposed in parallel, and thus, it is necessary to secure a large installation space for the plurality of spur gears. Accordingly, it is difficult to reduce (to realize compactification) a size of the entire liquid feeding device. Moreover, the slider which pushes reservoir plunger is formed in a cylindrical shape in which a female screw portion is formed an inner peripheral surface. Accordingly, a certain degree of diameter is required, and thus, a diameter of the slider easily increases. Therefore, in order to move the slider which easily increases in diameter in an axial direction of a feed screw, it is necessary to secure a large space around the feed screw to avoid an interference between the slider and the feed screw. Accordingly, a dead space increases, space efficiency deteriorates, and thus, it is difficult to decrease the size of the entire liquid feeding device.

The present invention is made in consideration of the above-described circumstance, and an object of thereof is to provide a feeding device and a portable dispensing device capable of stably and accurately feed-moving a movable shaft and decreasing sizes thereof.

(1) According to an aspect of the present invention, there is provided a feeding device, including a tubular body which has an inner peripheral surface on which a female screw portion is formed and is rotatably disposed around an axis; a movable shaft which has an outer peripheral surface on which a male screw portion is formed, is disposed inside the tubular body in a state where the male screw portion and the female screw portion are screwed to each other and rotations thereof around the axis are restricted, and is movable along a direction of the axis between a start position and an end position according to a rotation of the tubular body; a final gear which is provided in the tubular body; a drive unit which has the driving gear; a power transmission mechanism which has a plurality of intermediate gears and transmits a driving force from the driving gear to the final gear via the plurality of intermediate gears; and a biasing mechanism which is configured to apply a biasing force to the movable shaft along the direction of the axis, in which the movable shaft is configured to move such that a distal end portion of the movable shaft is separated from the tubular body according to a movement of the movable shaft from the start position to the end position, at least one of the plurality of intermediate gears is a two-stage gear having two gears whose diameters are different from each other, and the biasing mechanism is configured to apply the biasing force to the movable shaft from the end position toward the start position, and presses the male screw portion against the female screw portion to the start position side.

According to the feeding device of the present invention, the driving force from the drive unit can be transmitted to the final gear via the driving gear and the power transmission mechanism having the plurality of intermediate gears, and thus, the tubular body can be rotated around the axis. In the movable shaft disposed inside the tubular body, the male screw portion is screwed to the female screw portion of the tubular body in a state where the rotation of the movable shaft around the axis is restricted, and thus, the movable shaft is not rotated by the rotation of the tubular body. Therefore, the movable shaft can be linearly feed-moved along the direction of the axis from the start position toward the end position according to the rotation of the tubular body, and the distal end portion of the movable shaft can be gradually separated from the tubular body.

In particular, the movable shaft is always biased to the start position side by the biasing mechanism, and thus, the male screw portion and the female screw portion are screwed to each other in a state where the male screw portion is pressed against the female screw portion on the tubular body side to the start position side. Accordingly, the female screw portion and the male screw portion can be screwed together with little rattling, and occurrence of backlash in a fitting portion of the female screw portion and the male screw portion can be suppressed. Therefore, a rotational force of the tubular body can be efficiently transmitted to the movable shaft, and the movable shaft can be stably and accurately moved toward the end position side in response to the rotation of the tubular body. Therefore, for example, the movable shaft can be accurately feed-moved by a desired amount of movement from the start position to the end position. Accordingly, for example, in a case where liquid feeding is performed using the feed-movement of the movable shaft, it is possible to stably and accurately feed a desired amount of liquid.

Moreover, at least one of the plurality of intermediate gears is the two-stage gear. Therefore, compared to a case where a plurality of spur gears are combined with each other in parallel as in the related art, the driving force can be transmitted to the final gear while saving space is realized. Therefore, the power transmission mechanism can be designed compactly, and as a result, the entire feeding device can be reduced in size. Moreover, unlike the related art, by rotating the tubular body in which the female screw portion is formed, the movable shaft in which the male screw portion is formed and a decrease in the diameter is easily realized can be feed-moved. Accordingly, compared to the related art, it is possible to decrease the diameter size of the movable portion. Therefore, it is not necessary to secure a large movable space necessary for the movement of the movable shaft, and a dead space can be reduced correspondingly. Also in this respect, the entire feeding device can be reduced in size. In addition, it is possible to decrease the diameter of the tubular body itself, and thus, roundness of the tubular body is easily improved, and the movable shaft is easily held straightly along the axis with less inclination. Therefore, it is possible to stably feed-move the movable shaft with excellent straightness.

(2) The drive unit and the power transmission mechanism may be disposed to be arranged in a row along a virtual axis parallel to the axis, and may be disposed in parallel to the tubular body and the movable shaft.

In this case, the drive unit and the power transmission mechanism are disposed to be arranged in a row along the virtual axis. Moreover, the drive unit and the power transmission mechanism are disposed in parallel to the tubular body and the movable shaft, and thus, the drive unit, the power transmission mechanism, the tubular body, and the movable shaft can be disposed in a compact manner in a collected state. Accordingly, the entire feeding device can be easily reduced in size, and in particular, it is possible to effectively suppress an increase in size in the direction of the axis.

(3) The biasing mechanism may include a coil spring which is elastically deformable in the direction of the axis according to the movement of the movable shaft and biases the movable shaft toward the start position side by an elastic restoring force.

In this case, it is possible to bias the movable shaft by a simple method using only the elastic restoring force of the coil spring, and thus, a configuration can be easily simplified without adopting a complicated configuration. Moreover, the coil spring is elastically deformed according to the feed-movement of the movable shaft, and thus, the elastic restoring force increases as the movable shaft moves from the start position toward the end position. Therefore, the coil spring can bias the movable shaft strongly. Accordingly, for example, even when fitting portions of the female screw portion and the male screw portion decrease according to the feed-movement of the movable shaft, the male screw portion in a remaining fitting portion can be reliably pressed against the female screw portion to the start position side. Therefore, it is possible to effectively suppress occurrence of the backlash.

(4) The drive unit may be a stepping motor, and a gear ratio between the driving gear and the final gear may be adjusted by the plurality of intermediate gears such that the movable shaft moves by a screw pitch of the male screw portion when the stepping motor is driven by one step angle.

In this case, when the stepping motor is driven by one step angle, the movable shaft moves by a screw pitch of the male screw portion. Accordingly, the amount of feed-movement of the movable shaft can be controlled using the number of drive pulses. Accordingly, for example, it is particularly effective in a case where the liquid feeding is performed using the feed-movement of the movable shaft, and it is possible to accurately feed a minute amount of liquid. Further, since the stepping motor is used, the stepping motor can be stably stopped by own holding force even in a state where the drive pulse is not input. Therefore, the driving gear can be prevented from rotating unexpectedly, and as a result, the movable shaft can be prevented from moving unexpectedly.

(5) The stepping motor may have a torque characteristic in which a maximum rotational torque thereof is larger than a maximum elastic restoring force of the coil spring and a minimum rotational torque thereof is larger than a minimum elastic restoring force of the coil spring.

In this case, the movable shaft can be stably and reliably feed-moved against the elastic restoring force of the coil spring without being affected by a situation of the elastic deformation of the coil spring.

(6) The movable shaft may have a proximal end portion which is disposed to penetrate the tubular body and is disposed in a state of being exposed to an outside of the tubular body at the start position, and a detection sensor which is configured to detect the proximal end portion when the movable shaft is located at the start position may be disposed outside the proximal end portion of the movable shaft in the direction of the axis.

In this case, the proximal end portion of the movable shaft can be detected using the detection sensor, and thus, it is possible to accurately determine whether or not the movable shaft is located at the start position based on a detection result of the detection sensor. Accordingly, for example, after the movable shaft moves to the end position, the movable shaft can be moved to be returned to the start position reliably and rapidly. Therefore, thereafter, the feed-movement of the movable shaft can be started again from a state where the movable shaft is reliably located at the start position.

(7) According to another aspect of the present invention, there is provided a portable dispensing device including the feeding device; and a portable main body case which accommodates the feeding device, in which the main body case includes an accommodation case, the accommodation case accommodating a reservoir, which includes a reservoir barrel filled with a content and a reservoir plunger disposed to be slidable in the reservoir barrel and in which the content is extruded according to a movement of the reservoir plunger, in a state where the reservoir is coaxially disposed with the axis, and the distal end portion of the movable shaft is in contact with the reservoir plunger at the start position in a state where pushing is allowed.

According to the portable dispensing device of the present invention, after the reservoir filled with the content is accommodated in the accommodation case, the movable shaft feed-moves from the start position to the end position. Accordingly, the reservoir plunger can be pushed via the distal end portion of the movable shaft. Accordingly, the content (for example, gas, liquid, or the like) in the reservoir barrel can be extruded to the outside and dispensed by a pushing-in amount. In particular, as described above, the movable shaft can be accurately feed-moved by a desired amount of movement from the start position to the end position, and thus, it is possible to dispense the content from the inside of the reservoir by a desired amount. Accordingly, for example, the present invention can be suitably used for an insulin pump or the like which requires a predetermined amount of medicinal solution to be dispensed accurately and regularly.

According to the present invention, it is possible to feed-move the movable shaft stably and accurately, and to reduce the size. Therefore, for example, in a case where the liquid feeding or the like is performed using the movable shaft, it is possible to accurately feed a minute amount of liquid, and thus, the present invention can be appropriately used for a device that performs the liquid feeding.

DETAILED DESCRIPTION OF THE PREFERRED EMBODIMENTS

Hereinafter, embodiments of a feeding device and a portable dispensing device according to the present invention will be described with reference to the drawings. In the present embodiment, a case where the feeding device and the portable dispensing device are applied to a medicinal injection device which injects a medicinal solution into a body of a user will be described as an example.

Figure 1:
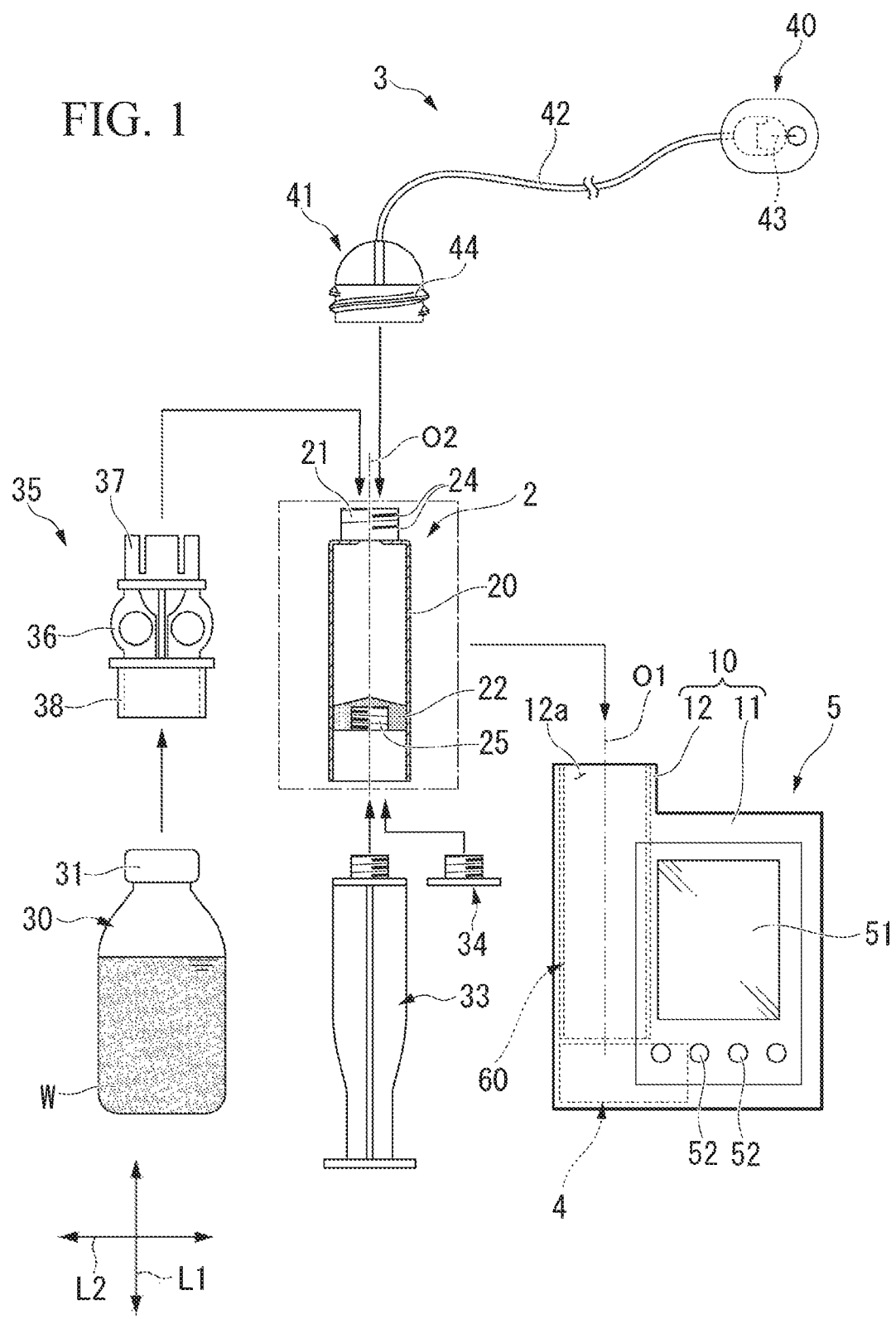
FIG. 1 is a diagram showing an embodiment of a feeding device and a liquid feeding device (portable dispensing device) according to the present invention, and is a configuration diagram showing a configuration of the entire medicinal injection device.

As shown in FIG. 1, a medicinal injection device 1 of the present embodiment includes a reservoir 2 which is filled with a medicinal solution W (content), an injection set 3 which injects the medicinal solution W dispensed from an inside of the reservoir 2 into the body of the user, and a liquid feeding device (portable dispensing device according to the present invention) 5 which includes a feeding device 4 therein, is mounted to be removable from the reservoir 2, and dispenses the medicinal solution W from the inside of the reservoir 2 using the feeding device 4. In addition, the medicinal solution W is not particularly limited, and for example, insulin may be mentioned. In this case, the liquid feeding device 5 functions as a so-called insulin pump.

The liquid feeding device 5 includes a main body case 10 which accommodates the feeding device 4 therein. The main body case 10 includes a main case 11 which is formed in a rectangular parallelepiped box shape, and an accommodation case 12 which is integrally formed with the main case 11 and removably accommodates the reservoir 2 therein. The accommodation case 12 is formed in a cylindrical shape which extends along a first axis (axis according to the present invention) O1, and an accommodation opening 12a which is open outward is formed on an end portion of the accommodation case 12. In addition, the main body case 10 will be described in detail later.

In the present embodiment, a direction along the first axis O1 of the accommodation case 12 is referred to as an upward-downward direction L1, a side of the accommodation opening 12a in the upward-downward direction L1 is referred to as an upper side, and a side opposite to the upper side is referred to as a lower side. In addition, in a plan view of the main body case 10, a direction orthogonal to the upward-downward direction L1 and a thickness direction of the main body case 10 is referred to as a right-left direction L2.

(Reservoir)

Figure 2:
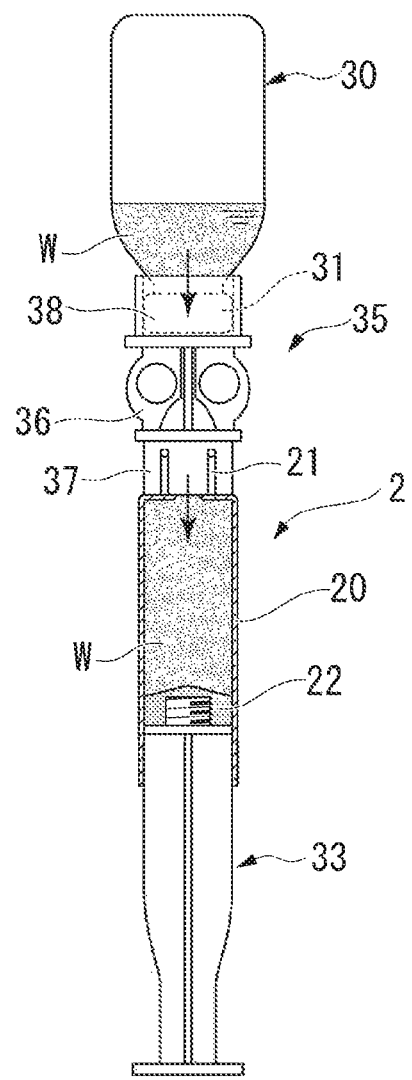
FIG. 2 is a diagram showing a state where a medicinal solution in a vial is transferred to a reservoir shown in FIG. 1 and fills the reservoir.
Figure 3:
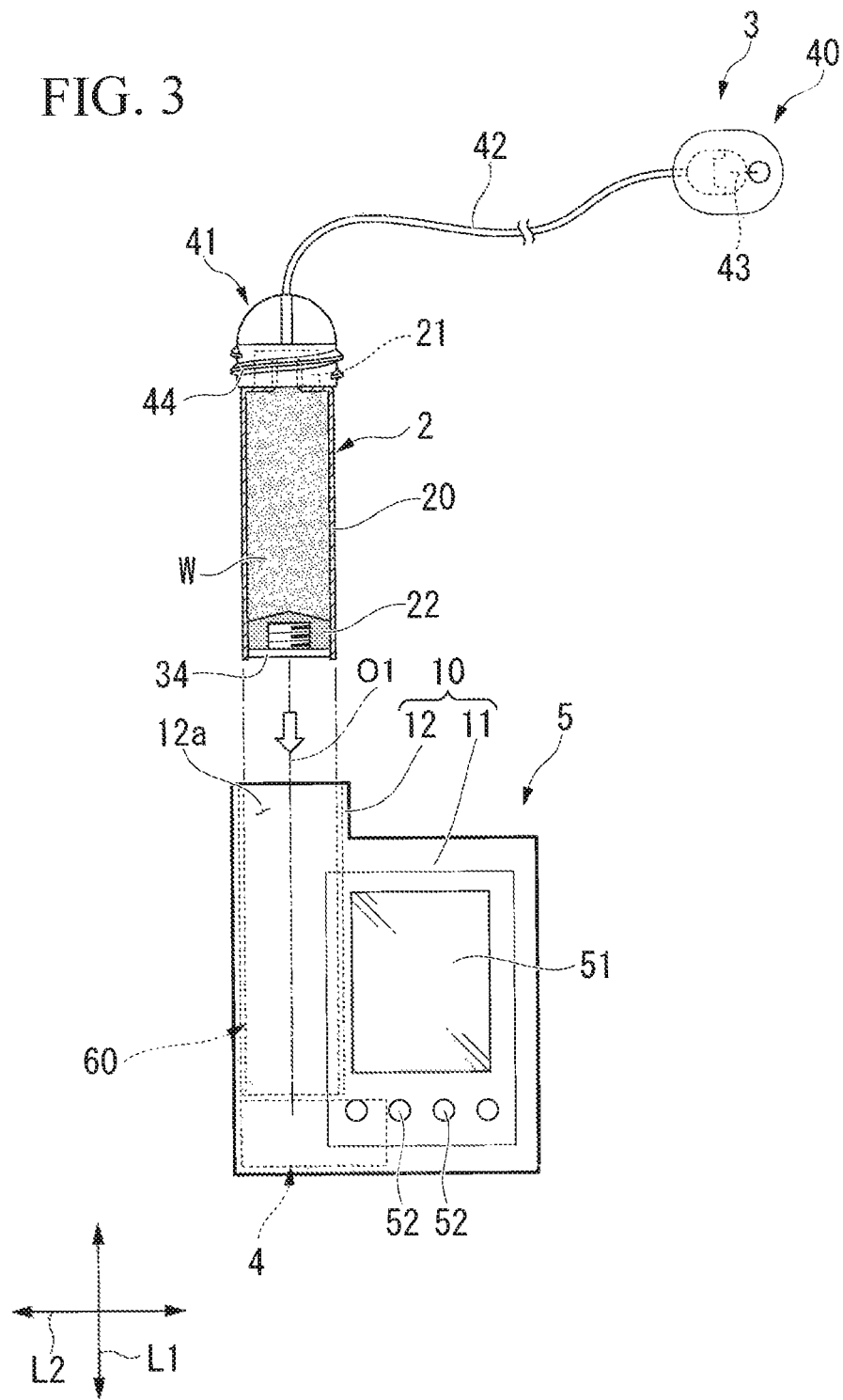
FIG. 3 is a diagram showing a state where the reservoir which is filled with the medicinal solution and on which an injection set is mounted is incorporated in an accommodation case of a liquid feeding device.

First, the reservoir 2 will be described briefly. As shown in FIGS. 1 to 3, the reservoir 2 is a so-called medicinal container, and includes a topped tubular reservoir barrel 20 having a mouth portion 21 and a reservoir plunger 22 which is slidably disposed in the reservoir barrel 20.

The reservoir barrel 20 is formed in a cylindrical shape which extends along the upward-downward direction L1 and is centered on a second axis O2, and an inside of the reservoir barrel 20 can be filled with the medicinal solution W. The mouth portion 21 is formed on an upper end portion side of the reservoir barrel 20, and an opening portion is formed on a lower end portion side of the reservoir barrel 20. Accordingly, the reservoir barrel 20 is open downward. For example, a sealing plug 23 (refer to FIG. 5) such as a rubber plug which closes the mouth portion 21 is provided inside the mouth portion 21. A connection screw portion 24 is formed over the entire periphery of an outer peripheral surface of the mouth portion 21.

The reservoir plunger 22 is inserted into the reservoir barrel 20 from below through the opening portion of the reservoir barrel 20. The reservoir plunger 22 can slide upward or downward in the reservoir barrel 20 along the second axis O2 in a state where the outer peripheral surface of the reservoir plunger 22 is contact with an inner peripheral surface of the reservoir barrel 20. In addition, a portion between the outer peripheral surface of the reservoir plunger 22 and the inner peripheral surface of the reservoir barrel 20 is tightly (liquid lightly, air tightly) sealed. Moreover, a connection screw hole 25 is formed in a lower surface of the reservoir plunger 22. However, the connection screw hole 25 is not essential and may not be provided.

The medicinal solution W is transferred or sucked up into the reservoir 2 configured as described above from a vial (or referred to as an ample) 30 filled with the medicinal solution W in advance and thus, the medicinal solution W can fill the reservoir 2.

In order to fill the medicinal solution W in the reservoir 2, a vial cap 35 serving as a relay cap can be mounted on the mouth portion 21 of the reservoir barrel 20. The vial cap 35 includes a cap body 36, a first mounting mouth portion 37 which is detachably mounted on the mouth portion 21 of the reservoir barrel 20, and a second mounting mouth portion 38 which is detachably mounted on a sealing cap 31 (for example, formed of rubber) of the vial 30. The first mounting mouth portion 37 and the second mounting mouth portion 38 are disposed on sides opposite to each other across the cap body 36, and are integrally formed with the cap body 36, respectively.

As shown in FIG. 2, for example, the first mounting mouth portion 37 can be mounted to surround the mouth portion 21 of the reservoir barrel 20 from the outside and can be mounted with one touch using the connection screw portion 24 formed on the mouth portion 21 side of the reservoir barrel 20. In addition, a needle (not shown) which punctures the sealing plug 23 and communicates with the inside of the reservoir barrel 20 is provided inside the first mounting mouth portion 37 when the first mounting mouth portion 37 is mounted on the mouth portion 21 of the reservoir barrel 20.

For example, the second mounting mouth portion 38 can be mounted with one touch so as to surround the sealing cap 31 of the vial 30 from the outside. Moreover, a needle (not shown) which punctures the sealing cap 31 and communicates with the inside of the vial 30 is provided inside the second mounting mouth portion 38 when the second mounting mouth portion 38 is mounted on the sealing cap 31 of the vial 30.

The needle on the first mounting mouth portion 37 side and the needle on the second mounting mouth portion 38 side communicate with each other through the cap body 36. Accordingly, by integrally combining the vial 30 and the reservoir 2 via the vial cap 35, the medicinal solution W in the vial 30 can be transferred or sucked up into the reservoir 2 through the vial cap 35 and can fill the inside of the reservoir 2. In addition, it is possible to connect an operation member 33 to the reservoir plunger 22 using the connection screw hole 25. Accordingly, it is possible to appropriately move the reservoir plunger 22 using the operation member 33, and the inside of the reservoir 2 can be appropriately filled with the medicinal solution W.

As described above, after the inside of the reservoir 2 is filed with the medicinal solution W, the vial cap 35 and the operation member 33 are not necessary, and thus, are removed from the reservoir 2. Thereafter, as shown in FIG. 3, after the injection set 3 is combined to the reservoir 2, the reservoir 2 is incorporated into the liquid feeding device 5. Moreover, when the reservoir 2 is incorporated into the liquid feeding device 5, for example, a cover plate 34 can be mounted on the reservoir plunger 22 using the connection screw hole 25.

(Injection Set)

Next, the injection set 3 will be briefly described. As shown in FIGS. 1 and 3, the injection set 3 includes an injection patch 40 which can be attached to a body surface of a user by sticking or the like, a relay connector 41 which can be mounted on the mouth portion 21 of the reservoir barrel 20, and a tube 42 which is connected between the relay connector 41 and the injection patch 40.

The injection patch 40 includes a plastic cannula-type indwelling needle 43 which can puncture the body of the user together with an inner needle (not shown) and is placed on the body surface by pulling out the inner needle. For example, the relay connector 41 can be mounted so as to surround the mouth portion 21 of the reservoir barrel 20 from the outside and can be mounted with one touch using the connection screw portion 24 which is formed on the mouth portion 21 side of the reservoir barrel 20. In addition, a needle (not shown) is provided inside the relay connector 41, and the needle punctures the sealing plug 23 and communicates with the inside of the reservoir barrel 20 when the relay connector 41 is mounted on the mouth portion 21 of the reservoir barrel 20. In addition, a first connection screw portion 44 is formed on an outer peripheral surface of the relay connector 41.

The tube 42 is a long tube having a flexibility and communicates with the needle and the indwelling needle 43. Accordingly, the medicinal solution W dispensed from the inside of the reservoir 2 can be injected into the body through the tube 42 and the indwelling needle 43.

(Liquid Feeding Device)

Figure 4:
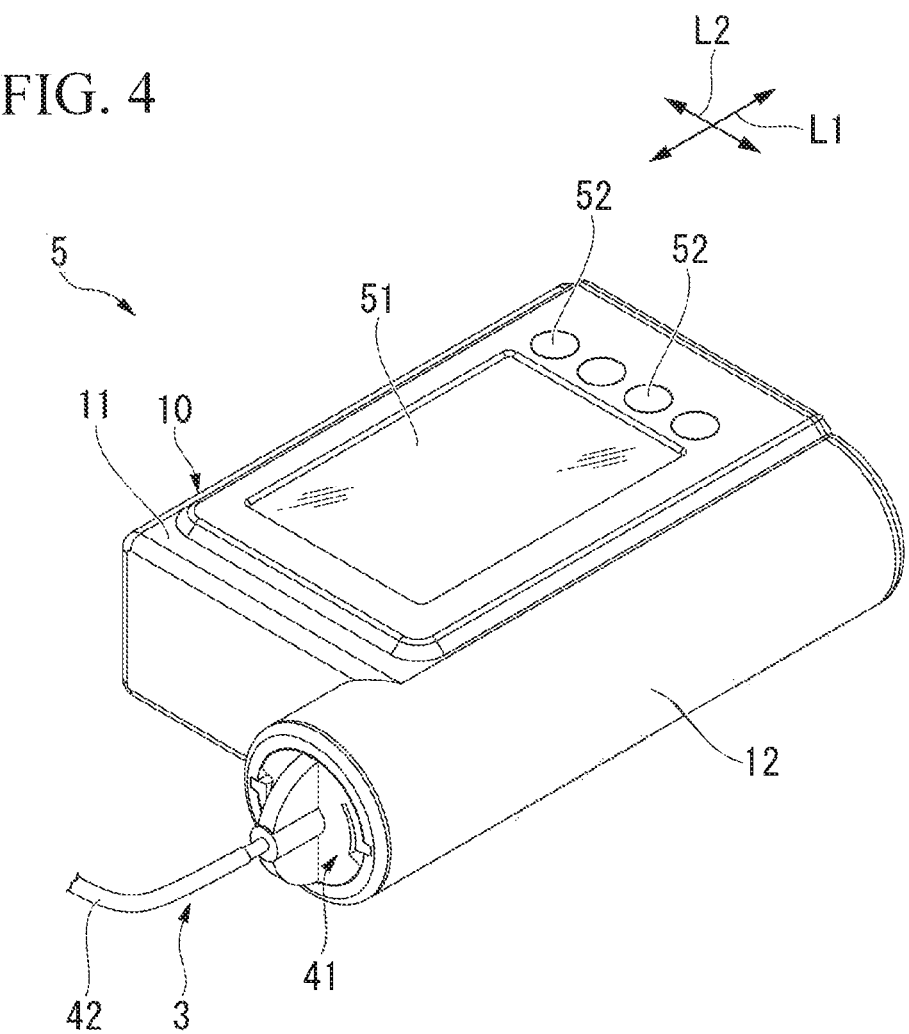
FIG. 4 is a perspective view showing the liquid feeding device in a state where the reservoir on which the injection set is mounted is set.
Figure 5:
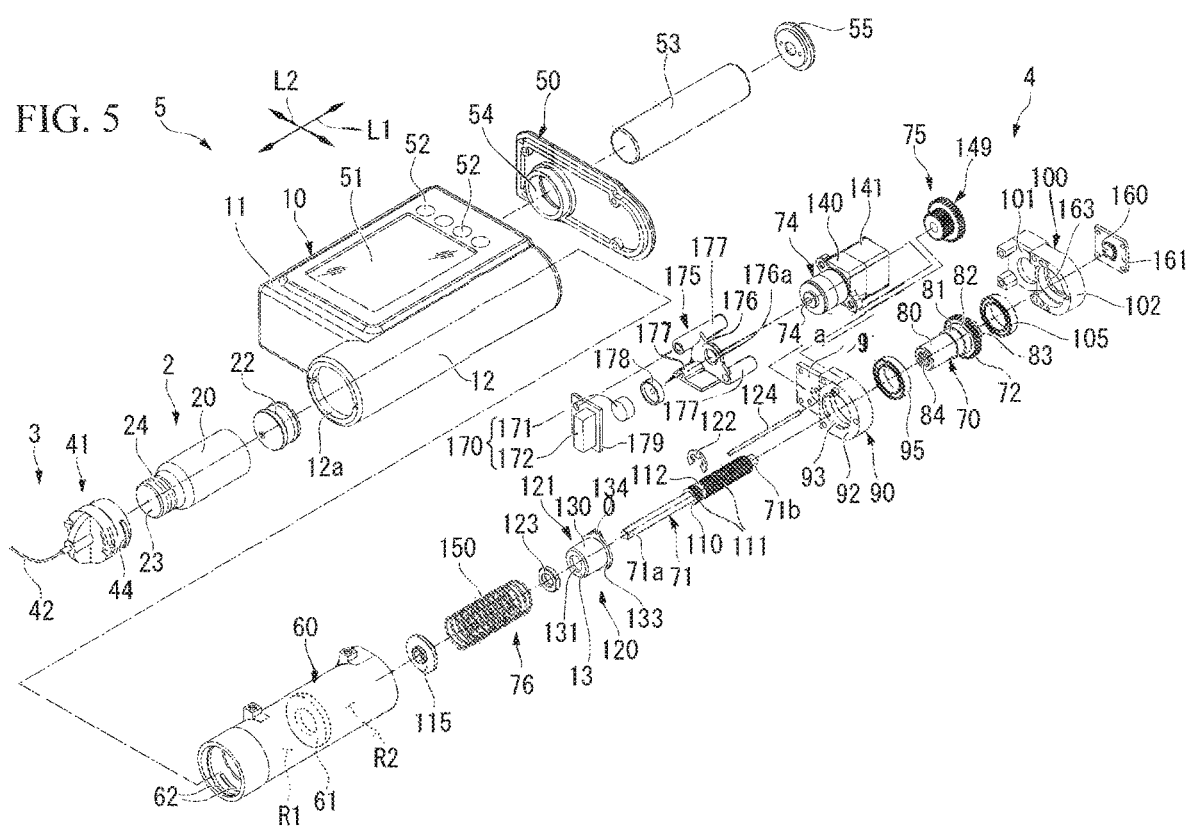
FIG. 5 is an exploded perspective view of the liquid feeding device shown in FIG. 4.

Next, the liquid feeding device 5 will be described. As shown in FIGS. 3 to 5, the liquid feeding device 5 includes the feeding device 4 which extrudes the medicinal solution W filling the inside of the reservoir 2 from the inside of the reservoir 2 and dispenses the medicinal solution W to the injection set 3 side, the main body case 10 which accommodates the feeding device therein, and a back plate 50 which is combined to the main body case 10.

As described above, the main body case 10 includes the main case 11 which is formed in a rectangular parallelepiped box shape and the accommodation case 12 which removably accommodates the reservoir 2, and is portable (can be carried). The main body case 10 is open downward, and the feeding device 4 or other various components can be assembled into the main body case 10 mainly from below.

For example, in addition to the feeding device 4, for example, a main circuit board is disposed in the main body case 10, and a control unit such as a CPU which comprehensively controls the entire liquid feeding device 5 and various storage units such as a flash memory are mounted on the main circuit board. Furthermore, in the main body case 10 for example, a display unit 51 which displays various information related to an operation of the liquid feeding device 5 or various information related to liquid feeding, an input unit 52 such as an input button which can be operated to input, and a power supply unit 53 which supplies power to various components are provided. In addition, for example, the display unit 51 and the input unit 52 are disposed to be exposed to a front side of the main case 11. For example, the power supply unit 53 is a replaceable primary battery such as a button battery or a dry battery, a chargeable/dischargeable secondary battery, or the like. In the shown example, a dry cell type power supply unit 53 is taken as an example.

The back plate 50 is assembled to the main body case 10 using a fastening member such as a connection screw (not shown), and thus, closes the main body case 10. Moreover, an exchange window 54 for exchanging the power supply unit 53 is formed in the back plate 50. The exchange window 54 is closed by a battery cap 55 attached to the back plate 50.

The accommodation case 12 is formed so as to protrude upward from the main case 11, and an accommodation opening 12a is formed on an upper end portion side of the accommodation case 12. Accordingly, the reservoir 2 can be incorporated to be inserted into the accommodation case 12 through the accommodation opening 12a from above. Specifically, the reservoir 2 can be accommodated in an inner case 60 disposed inside the accommodation case 12.

Figure 6:
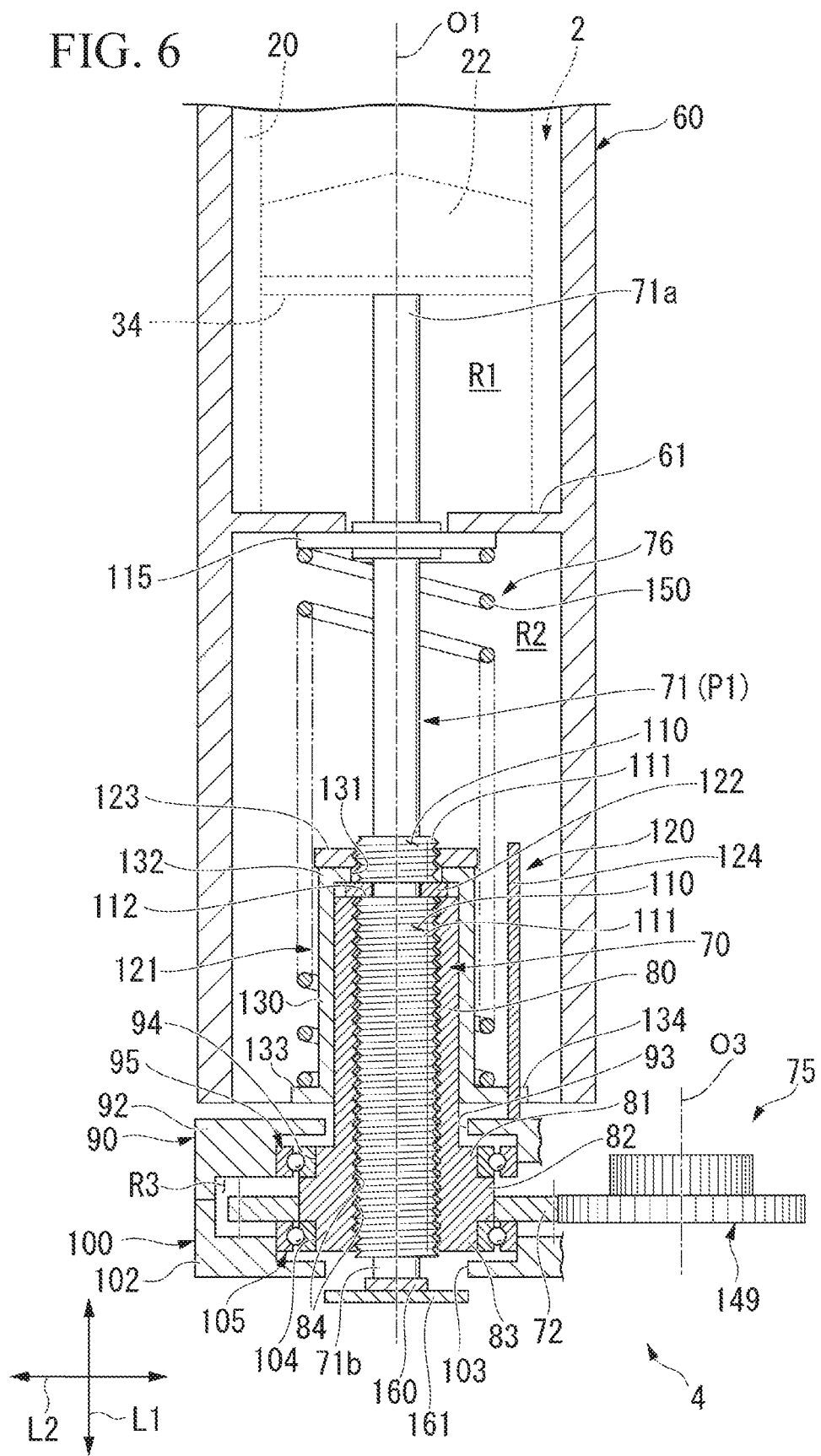
FIG. 6 is a longitudinal sectional view of the feeding device shown in FIG. 5 and a longitudinal sectional view showing a state where a plunger screw is located at a start position.

As shown in FIGS. 5 and 6, the inner case 60 is formed in a cylindrical shape having an inner diameter larger than an outer diameter of the reservoir barrel 20 and is fixed to an inner side of the accommodation case 12 in a state of being coaxially disposed with the first axis O1. The inner case 60 is formed so as to extend along the upward-downward direction L1 and is incorporated into the accommodation case 12 from a lower side of the accommodation case 12. Moreover, a length (full length) of the inner case 60 along the upward-downward direction L1 is longer than a full length of the reservoir 2 and shorter than a full length of the accommodation case 12.

An annular stopper ring 61 with which a lower end portion of the reservoir barrel 20 comes into contact is formed in the inner case 60. Accordingly, the reservoir 2 accommodated in the inner case 60 can be stably supported using the stopper ring 61. Moreover, a second connection screw portion 62 is formed on the inner peripheral surface of the inner case 60 on the upper end portion side, and the first connection screw portion 44 formed on the relay connector 41 is screwed to the second connection screw portion 62. Accordingly, when the reservoir 2 on which the injection set 3 is mounted is accommodated in the inner case 60, the reservoir 2 is inserted into the inner case 60 while being screwed, and thus, the first connection screw portion 44 and the second connection screw portion 62 can be screwed to each other. Accordingly, as shown in FIG. 4, the entire reservoir 2 including the relay connector 41 can be accommodated in the inner case 60, and thus, can be prevented from coming off upward.

As shown in FIGS. 5 and 6, a space located above the stopper ring 61 in an inner space of the inner case 60 is an upper accommodation space R1 for accommodating the reservoir 2. A space located below the stopper ring 61 in the inner space of the inner case 60 is a lower accommodation space R2 for incorporating a portion of the feeding device 4.

For example, a mounting member such as a clip or a mounting belt (not shown) can be combined with the main body case 10 configured as described above. Therefore, it is possible to stably mount the main body case 10 at a predetermined mounting location (for example, around a waist) of the user via the mounting member.

(Feeding Device)

Figure 7:
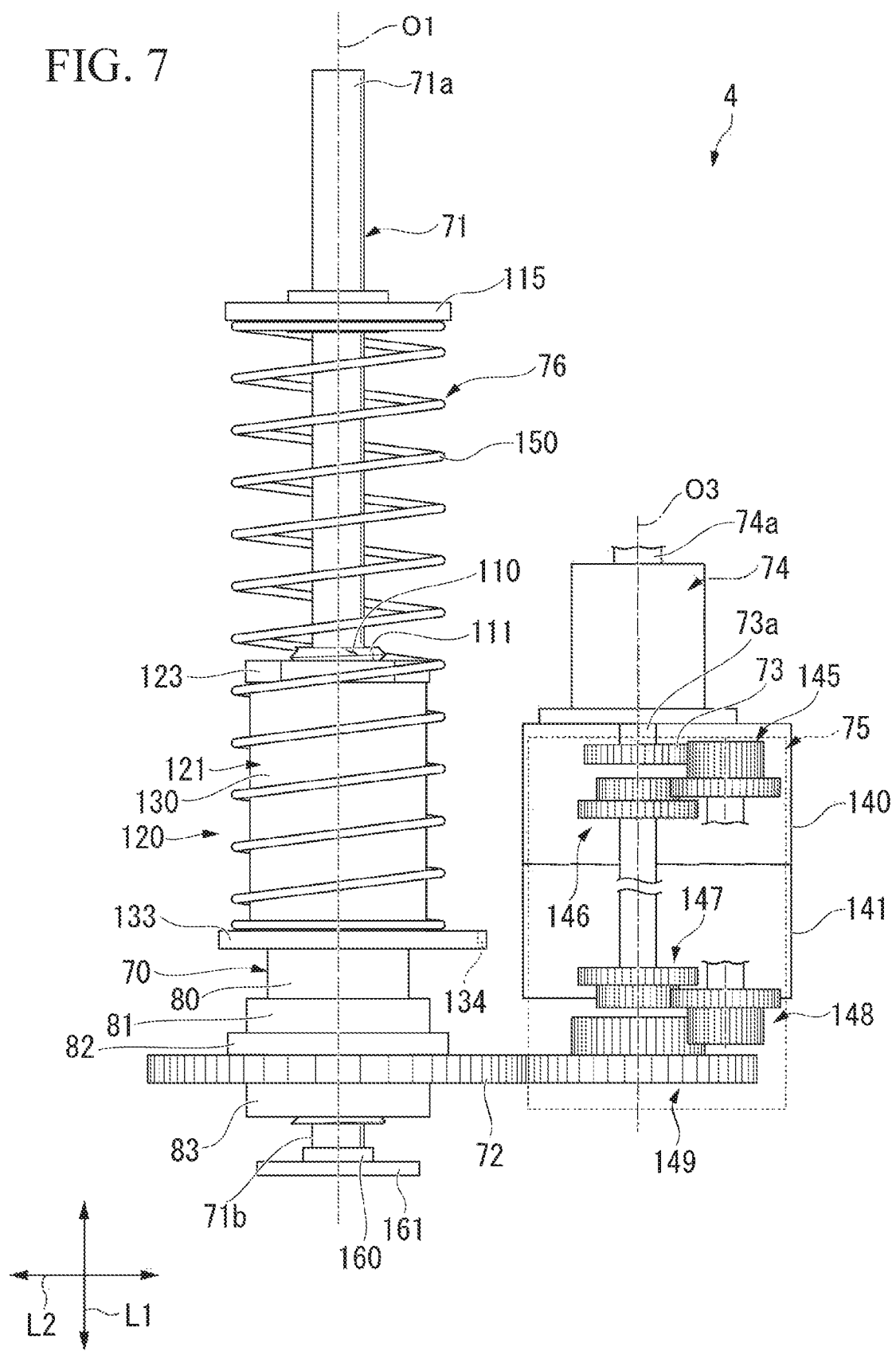
FIG. 7 is a side view of the feeding device shown in FIG. 6.
Figure 8:
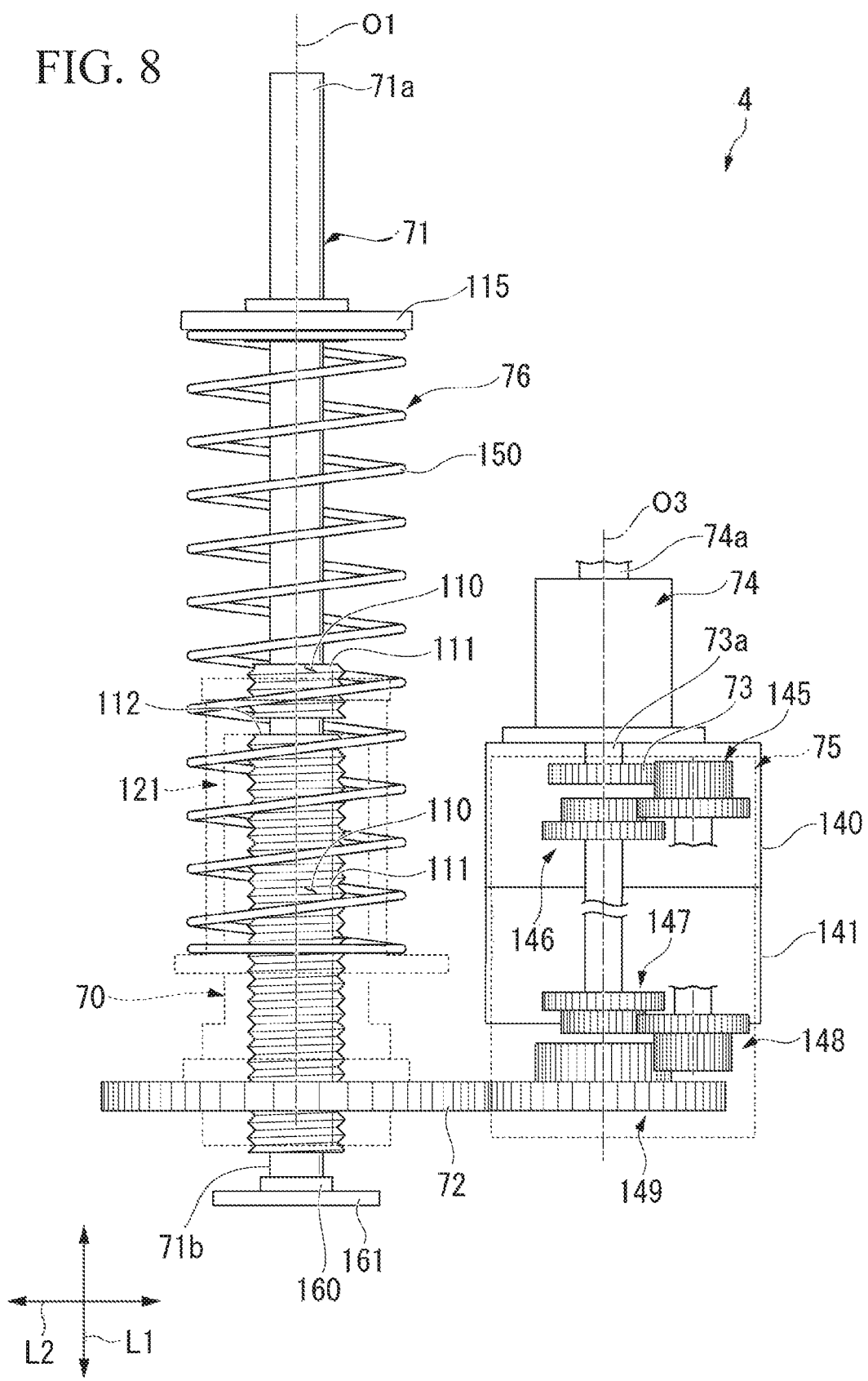
FIG. 8 is a side view showing a state where a guide collar and a rotating cylinder are removed from the state shown in FIG. 7.

As shown in FIGS. 5 to 7, the feeding device 4 includes a rotating cylinder (tubular body according to the present invention) 70 which is rotatably disposed around the first axis O1, a plunger screw (movable shaft according to the present invention) 71 which is disposed inside the rotating cylinder 70 and can move in the upward-downward direction L1 between a start position P1 (refer to FIG. 6) and an end position P2 (refer to FIG. 10) according to a rotation of the rotating cylinder 70, a final gear 72 which is provided in the rotating cylinder 70, a stepping motor (drive unit according to the present invention) 74 which has a driving gear 73, a power transmission mechanism 75 which has a plurality of intermediate gears and transmits a driving force (rotational power) from the driving gear 73 to the final gear 72 via the plurality of intermediate gears, and a biasing mechanism 76 which is configured to apply a biasing force to the plunger screw 71 along the upward-downward direction L1.

Moreover, in the present embodiment, in a plan view when viewed in the upward-downward direction L1, a direction intersecting the first axis O1 is referred to as a radial direction, and a direction around the first axis O1 is referred to as a circumferential direction.

The rotating cylinder 70 is formed in a multi-stage tubular shape whose diameter is changed stepwise in the upward-downward direction L1, and is open upward and downward. Specifically, the rotating cylinder 70 includes a first rotating cylinder portion 80 which has a smallest outer diameter, a second rotating cylinder portion 81 which has an outer diameter larger than that of the first rotating cylinder portion 80, a third rotating cylinder portion 82 which has an outer diameter larger than that of the second rotating cylinder portion 81, and a fourth rotating cylinder portion 83 which has the same outer diameter as that of the second rotating cylinder portion 81. The first rotating cylinder portion 80, the second rotating cylinder portion 81, the third rotating cylinder portion 82, and the fourth rotating cylinder portion 83 are disposed in this order from above, and thus, the rotating cylinder 70 is formed in a multi-stage tubular shape. However, the shape of the rotating cylinder 70 is not limited to this.

The first rotating cylinder portion 80 is formed to be longer in the upward-downward direction L1 than the second rotating cylinder portion 81, the third rotating cylinder portion 82, and the fourth rotating cylinder portion 83, and functions as a guide member which guides a guide collar 121 described later. In the rotating cylinder 70, the first rotating cylinder portion 80 enters the lower accommodation space R2 of the inner case 60 from below, and the rotating cylinder 70 is disposed in the is main body case 10 such that the second rotating cylinder portion 81, the third rotating cylinder portion 82, and the fourth rotating cylinder portion 83 are disposed below the inner case 60. In addition, a female screw portion 84 is formed on an inner peripheral surface of the rotating cylinder 70 over the entire length thereof.

The final gear 72 is provided in the third rotating cylinder portion 82 of the rotating cylinder 70. Moreover, the final gear 72 may be integrally formed with the rotating cylinder 70, may be separately formed from the rotating cylinder 70, or, for example, may be integrally combined by being fitted to an outer peripheral surface of the third rotating cylinder portion 82.

As shown in FIGS. 5 and 6, the rotating cylinder 70 configured as described above is rotatably supported around the first axis O1 by a first gear plate 90 and a second gear plate 100 disposed below the inner case 60. Moreover, in FIG. 7, the first gear plate 90 and the second gear plate 100 are not shown.

The first gear plate 90 and the second gear plate 100 are integrally combined with each other in a state where the first gear plate 90 overlaps the second gear plate 100. An installation space R3 is formed inside the first gear plate 90 and the second gear plate 100 which are integrally combined with each other. The rotating cylinder 70 is rotatably supported around the first axis O1 by a first bearing 95 and a second bearing 105 mainly in a state where the second rotating cylinder portion 81, the third rotating cylinder portion 82, and the fourth rotating cylinder portion 83 are accommodated in the installation space R3.

The first gear plate 90 includes a first plate 91 and a first support frame 92, the first plate 91 and the first support frame 92 are integrally formed in a state of being arranged in the right-left direction L2, and the first gear plate 90 is disposed below the inner case 60. In the first support frame 92, a first through-hole 93 into which the first rotating cylinder portion 80 is inserted and which has a circular shape in a plan view, and a first surrounding wall 94 which surrounds the second rotating cylinder portion 81 from the outside in the radial direction are formed. The first through-hole 93 is formed to have a diameter larger than an outer diameter of the first rotating cylinder portion 80 and is coaxially disposed with the first axis O1.

The first bearing 95 is fixed between the second rotating cylinder portion 81 and the first surrounding wall 94. For example, the first bearing 95 is a ball bearing, an inner ring of the first bearing 95 is closely fitted to an outer peripheral surface of the second rotating cylinder portion 81, and an outer ring of the first bearing 95 is closely fitted to an inner peripheral surface of the first surrounding wall 94. Accordingly, the first bearing 95 is fixed between the second rotating cylinder portion 81 and the first surrounding wall 94.

The second gear plate 100 includes a second plate 101 and a second support frame 102, the second plate 101 and the second support frame 102 are integrally formed with each other in a state of being arranged in the right-left direction L2, and the second gear plate 100 is disposed below the first gear plate 90. In the second support frame 102, a second through-hole 103 into which the plunger screw 71 is inserted and which has a circular shape in a plan view, and a second surrounding wall 104 which surrounds the fourth rotating cylinder portion 83 from the outside in the radial direction are formed. For example, the second through-hole 103 is formed to have the same diameter as that of the first through-hole 93, and is coaxially disposed with the first axis O1.

The second bearing 105 is fixed between the fourth rotating cylinder portion 83 and the second surrounding wall 104. For example, the second bearing 105 is a ball bearing, an inner ring of the second bearing 105 is closely fitted to an outer peripheral surface of the fourth rotating cylinder portion 83, and an outer ring of the second bearing 105 is closely fitted to an inner peripheral surface of the second surrounding wall 104. Accordingly, the second bearing 105 is fixed between the fourth rotating cylinder portion 83 and the second surrounding wall 104.

The rotating cylinder 70 configured as described above is pivotally supported by the first gear plate 90 and the second gear plate 100 via the first bearing 95 and the second bearing 105, and thus, the rotating cylinder 70 can be rotated around the first axis O1 in a state of being stably supported with little rattling.

As shown in FIGS. 5 to 8, the plunger screw 71 is formed to be longer than the rotating cylinder 70 in the upward-downward direction L1, and is coaxially disposed with the first axis O1 to penetrate the rotating cylinder 70 up and down. At the start position P1, the plunger screw 71 extends upward so as to enter the upper accommodation space R1 of the inner case 60 beyond the stopper ring 61. In addition, a distal end portion (upper end portion) 71a of the plunger screw 71 can come into contact with the reservoir plunger 22 of the reservoir 2 so as to push the reservoir plunger 22 from below. In addition, at the start position P1, a proximal end portion (lower end portion) 71b of the plunger screw 71 is disposed in a state of being exposed downward from the rotating cylinder 70.

In the plunger screw 71, a portion of the plunger screw 71 which enters the rotating cylinder 70 at the start position P1 is an enlarged diameter portion 110 having a diameter larger than those of other portions of the plunger screw 71. A male screw portion 111 which is screwed to the female screw portion 84 formed on the rotating cylinder 70 side is formed on an outer peripheral surface of the enlarged diameter portion 110. In the shown example, the enlarged diameter portion 110 and the male screw portion 111 are formed to protrude upward from the rotating cylinder 70. Moreover, an annular groove portion 112 is formed in a portion of the enlarged diameter portion 110 located above the upper end portion of the rotating cylinder 70. Thereby, the enlarged diameter portion 110 and the male screw portion 111 are divided up and down across the groove portion 112.

The plunger screw 71 configured as described above is disposed inside the rotating cylinder 70 in a state where the male screw portion 111 and the female screw portion 84 are screwed to each other and a rotation around the first axis O1 is restricted by a rotation restricting mechanism 120 described later. Accordingly, the plunger screw 71 can move up or down between the start position P1 and the end position P2 according to the rotation of the rotating cylinder 70. The plunger screw 71 moves upward according to the movement from the start position P1 to the end position P2, and thus, the distal end portion 71a is gradually separated from the rotating cylinder 70. Therefore, the plunger screw 71 moves so as to extend from the rotating cylinder 70, and the reservoir plunger 22 can be pushed into (pushed up) the reservoir 2.

Moreover, the plunger screw 71 is inserted through an annular plunger bush 115 disposed coaxially with the first axis O1, and is movably guided by the plunger bush 115. The plunger bush 115 is disposed in the lower accommodation space R2 of the inner case 60 in a state where the plunger bush 115 is in contact with the stopper ring 61 from below. The plunger screw 71 is guided by the plunger bush 115, and thus, can move stably along the first axis O1 with less rattling.

As shown in FIGS. 5 to 7, the rotation restricting mechanism 120 includes a topped tubular guide collar 121 which surrounds the first rotating cylinder portion 80 from the outside in the radial direction, an E ring 122 and a connection nut 123 for integrally connecting the guide collar 121 to the plunger screw 71, and a guide shaft 124 which movably guides the guide collar 121 up or down in a state where a rotation of the guide collar 121 around the first axis O1 is restricted. Moreover, in FIG. 7, the guide shaft 124 is not shown.

The E ring 122 is fitted into the groove portion 112 formed in the plunger screw 71, and thus, is integrally combined with the plunger screw 71. The guide collar 121 includes a collar tube 130 which surrounds the first rotating cylinder portion 80 from the outside in the radial direction, a top wall portion 132 which closes an upper end portion of the collar tube 130 and has an insertion hole 131 into which the plunger screw 71 is inserted, and an annular flange piece 133 which protrudes radially outward from a lower end portion of the collar tube 130.

For example, an inner peripheral surface of the collar tube 130 is in sliding contact with or is in close contact with the outer peripheral surface of the first rotating cylinder portion 80. The top wall portion 132 is located above the E ring 122. Accordingly, the guide collar 121 is attached to cover the first rotating cylinder portion 80 from above in a state where the guide collar 121 is placed on the E ring 122.

The connection nut 123 is screwed to a portion of the male screw portion 111 of the plunger screw 71 which is located above the E ring 122, and is tightened so that the top wall portion 132 is interposed between the E ring 122 and the connection nut 123. Accordingly, the guide collar 121 is integrally connected to the plunger screw 71 together with the E ring 122 and the connection nut 123.

The guide shaft 124 is erected on the first support frame 92 so as to extend upward from the first support frame 92 in the first gear plate 90. The guide shaft 124 is disposed so as to pass in the vicinity of the flange piece 133 of the guide collar 121 and is formed to extend upward from the rotating cylinder 70. Moreover, a bifurcated guide piece 134 which protrudes outward in the radial direction and is in contact with the guide shaft 124 in the circumferential direction is formed in a portion of the flange piece 133 in the guide collar 121. The guide piece 134 is in contact with the guide shaft 124, and thus, a circumferential movement of the guide collar 121 is restricted. Accordingly, a rotation of the guide collar 121 around the first axis O1 is restricted.

Accordingly, the plunger screw 71 with which the guide collar 121 is integrally combined is restrained from rotating around the first axis O1, and thus, the plunger screw 71 can move in the upward-downward direction L1 according to the rotation of the rotating cylinder 70. The guide piece 134 moves up or down while being guided by the guide shaft 124 according to the movement of the plunger screw 71. Moreover, a position at which the flange piece 133 in the guide collar 121 moves to the vicinity of the upper end portion of the first rotating cylinder portion 80 is the end position P2 of the plunger screw 71 (refer to FIG. 10).

As shown in FIGS. 5 to 7, the stepping motor 74 and the power transmission mechanisms 75 are disposed to be arranged up or down in a row along a virtual axis O3 parallel to the first axis O1, and are disposed in parallel to the rotating cylinder 70 and the plunger screw 71. Moreover, in FIG. 6, the stepping motor 74 is not shown, and a portion of the power transmission mechanism 75 is not shown.

The stepping motor 74 is attached on a motor spacer 140. The motor spacer 140 is attached to overlap a gear box 141 which is attached to the first plate 91 in the first gear plate 90. The stepping motor 74 is attached to the motor spacer 140 in a state where a drive shaft 73a to which the driving gear 73 is connected faces downward. Accordingly, the drive shaft 73a and the driving gear 73 are accommodated in the motor spacer 140.

Moreover, in the main body case 10, a motor control unit (not shown) which outputs a driving pulse based on an instruction from the control unit and a driver (not shown) which supplies a control current based on the driving pulse to the stepping motor 74 are provided. Accordingly, for example, a rotational speed, a rotation angle, or the like of the stepping motor 74 is controlled.

As described above, the power transmission mechanism 75 includes the plurality of intermediate gears, and transmits a driving force of the stepping motor 74 from the driving gear 73 to the final gear 72 by meshing the plurality of intermediate gears with each other. At least one of the plurality of intermediate gears is a two-stage gear having two gears having different diameters. In the present embodiment, five intermediate gears are provided, and all of the five intermediate gears are two-stage gears 145 to 149.

Specifically, as shown in FIG. 7, the power transmission mechanism 75 includes the first two-stage gear 145 which meshes with the driving gear 73, the second two-stage gear 146 which meshes with the first two-stage gear 145, the third two-stage gear 147 which is formed on a connection shaft connected to the second two-stage gear 146, the fourth two-stage gear 148 meshing with the third two-stage gear 147, and the fifth two-stage gear 149 which meshes with the fourth two-stage gear 148 and meshes with the final gear 72.

The five two-stage gears 145 to 149 mesh with each other in a state where the five two-stage gears 145 to 149 are adjusted such that a gear ratio between the driving gear 73 and the final gear 72 is a predetermined gear ratio. Specifically, when the stepping motor 74 is driven by one step angle, the gear ratio between the driving gear 73 and the final gear 72 is adjusted by the five two-stage gears 145 to 149 so that the plunger screw 71 moves by a screw pitch of the male screw portion 111. In addition, in the five two-stage gears 145 to 149 described above, the four two-stage gears 145 to 148 except for the fifth two-stage gear 149 are disposed in the motor spacer 140 and the gear box 141. The fifth two-stage gear 149 is disposed in the installation space R3 between the first gear plate 90 and the second gear plate 100.

As shown in FIGS. 5 to 7, the biasing mechanism 76 has a coil spring 150. The biasing mechanism 76 applies a biasing force to the plunger screw 71 in a direction from the end position P2 to the start position P1, that is, downward using the coil spring 150, and thus, the male screw portion 111 is pressed against the female screw portion 84 to the start position P1 side.

The coil spring 150 is disposed to surround the guide collar 121 from the outside in the radial direction, and is coaxially disposed with the first axis O1 in a state of being compressed between the plunger bush 115 and the flange piece 133. Accordingly, the coil spring 150 can be elastically deformed according to the movement of the plunger screw 71. The coil spring 150 can bias the plunger screw 71 to the start position P1 side by biasing the guide collar 121 downward by an elastic restoring force.

Moreover, the guide collar 121, the E ring 122, and the connection nut 123 also play a role of transmitting the elastic restoring force of the coil spring 150 to the plunger screw 71, and thus, also function as components which constitute the biasing mechanism 76.

Figure 9:
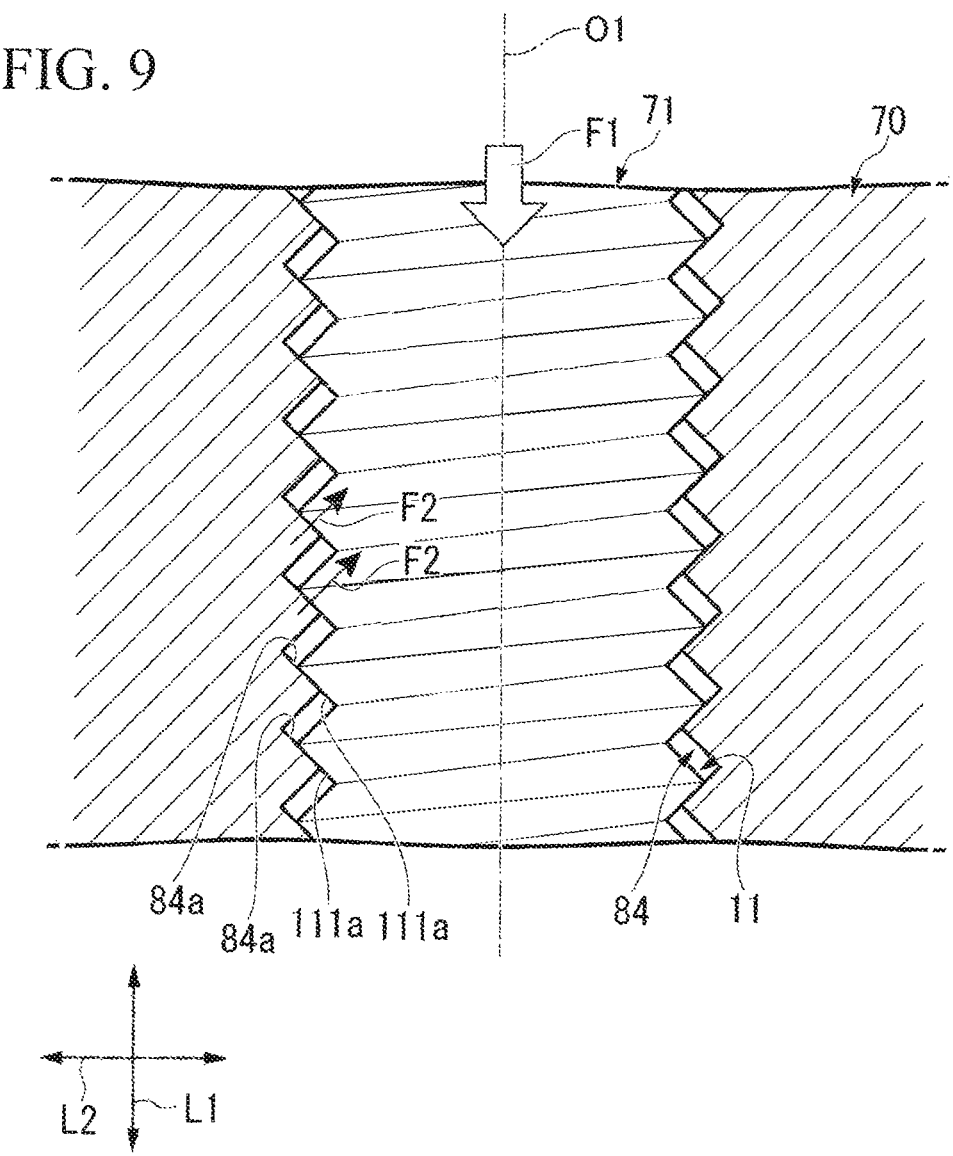
FIG. 9 is an enlarged view showing a fitting portion between a female screw portion of the rotating cylinder and a male screw portion of a plunger screw shown in FIG. 6.

The male screw portion 111 is pressed against the female screw portion 84 to the start position P1 side by the biasing mechanism 76. Accordingly, as shown in FIG. 9, lower flank surfaces 111a, facing downward of screw threads of the male screw portion 111 are pressed to upper flank surfaces 84a facing upward among the screw threads of the female screw portion 84, and the flank surfaces 84a and 111a are in close contact with each other without gap. Moreover, the stepping motor 74 has a torque characteristic in which a maximum rotational torque thereof is larger than a maximum elastic restoring force of the coil spring 150 and a minimum rotational torque thereof is larger than a minimum elastic restoring force of the coil spring 150.

Moreover, as shown in FIGS. 5 to 7, the feeding device 4 includes a detection sensor 160 which detects the proximal end portion 71b of the plunger screw 71 and a rotation sensor 170 which detects a rotating speed of the stepping motor 74 when the plunger screw 71 is located at the start position P1. Moreover, in FIGS. 6 and 7, the rotation sensor 170 and a sensor substrate holder 175 described later are not shown.

For example, the detection sensor 160 is a contact-type displacement sensor 160, disposed below the proximal end portion 71*b* of the plunger screw 71, and mounted on a switch board 161. The contact-type displacement sensor 160 is displaced by being pressed by the proximal end portion 71*b* of the plunger screw 71, and outputs a detection signal to the control unit. Moreover, the contact-type displacement sensor 160 is disposed at the position pressed by the proximal end portion 71*b* of the plunger screw 71, when the plunger screw 71 is located at the start position P1. Thereby, based on presence or absence of the detection signal, it is possible to detect whether or not the plunger screw 71 is located at the start position P1.

As shown in FIG. 5, for example, the rotation sensor 170 is an absolute type magnetic sensor, and includes a magnet (magnetic body) 171 which is attached to the stepping motor 74 side and in which S and N poles are alternately magnetized in a circumferential direction, and a sensor unit 172 which is a magneto-resistive element whose resistance value changes in response to a change in a magnetic field. The rotation sensor 170 is attached using a sensor substrate holder 175 which is disposed above the stepping motor 74 and is integrally combined with the motor spacer 140 with the stepping motor 74 disposed therebetween.

The sensor substrate holder 175 includes a holder plate 176 which is disposed above the stepping motor 74 and in which a through-hole 176*a* is formed, and a plurality of leg portions 177 which are integrated with the holder plate 176 and extend in the upward-downward direction L1. Lower end portions of the plurality of leg portions 177 are in contact with the motor spacer 140 from above and are combined with motor spacer 140. Upper end portions of the plurality of leg portions 177 are located above the holder plate 176.

The stepping motor 74 includes an auxiliary shaft 74*a* which extends upward and rotates together with the drive shaft 73*a*. The auxiliary shaft 74*a* passes through the through-hole 176*a* and extends upward from the holder plate 176. Moreover, a magnet holder 178 which rotatably holds the magnet 171 is fixed to the holder plate 176. The auxiliary shaft 74*a* penetrates the magnet holder 178, and thereafter, is integrally connected to the magnet 171. Accordingly, the magnet 171 can be rotated according to the rotation of the stepping motor 74.

The sensor unit 172 is mounted on a sensor board 179 which is supported by the upper end portions of the plurality of leg portions 177. A resistance value of the sensor unit 172 is changed through the sensor board 179 in accordance with a change of a magnetic field accompanying the rotation of the magnet 171. Therefore, the sensor unit 172 can detect the rotating speed of the stepping motor 74 based on the change in the resistance value, and outputs a detection result to the control unit. As described above, when the stepping motor 74 is driven by one step angle, the plunger screw 71 is adjusted so as to move by a screw pitch of the male screw portion 111. Therefore, the control unit can calculate the amount of movement of the plunger screw 71 based on the rotation speed of the stepping motor 74. Accordingly, for example, the control unit can detect that the plunger screw 71 moves from the start position P1 to the end position P2.

(Effect of Chemical Injection Device)

Next, a case where the medicinal solution W is injected into the body of the user using the medicinal injection device 1 configured as described above will be described.

In this case, in an initial state, as shown in FIGS. 4 and 6, the reservoir 2 which is filled with the medicinal solution W and on which the injection set 3 is mounted is set into the inner case 60 of the liquid feeding device 5. In this case, the reservoir 2 is appropriately prevented from coming off by the relay connector 41. Furthermore, the liquid feeding device 5 is appropriately attached to an attachment location of the user, the injection patch 40 of the injection set 3 is attached to the body surface of the user, and the indwelling needle 43 is placed on the body surface in a state of puncturing the body. In addition, the plunger screw 71 is positioned at the start position P1, and the distal end portion 71*a* of the plunger screw 71 is in contact with the reservoir plunger 22 of the reservoir 2 so that the plunger screw 71 can be pushed in from below.

When the stepping motor 74 is driven under the above-described initial state, the driving gear 73 rotates, and the five two-stage gears 145 to 149 and the final gear 72 can be sequentially rotated according to the rotation of the driving gear 73. Therefore, the driving force from the stepping motor 74 can be transmitted to the final gear 72 via the driving gear 73 and the five two-stage gears 145 to 149, and thus, the rotating cylinder 70 can be rotated around the first axis O1.

Figure 10:
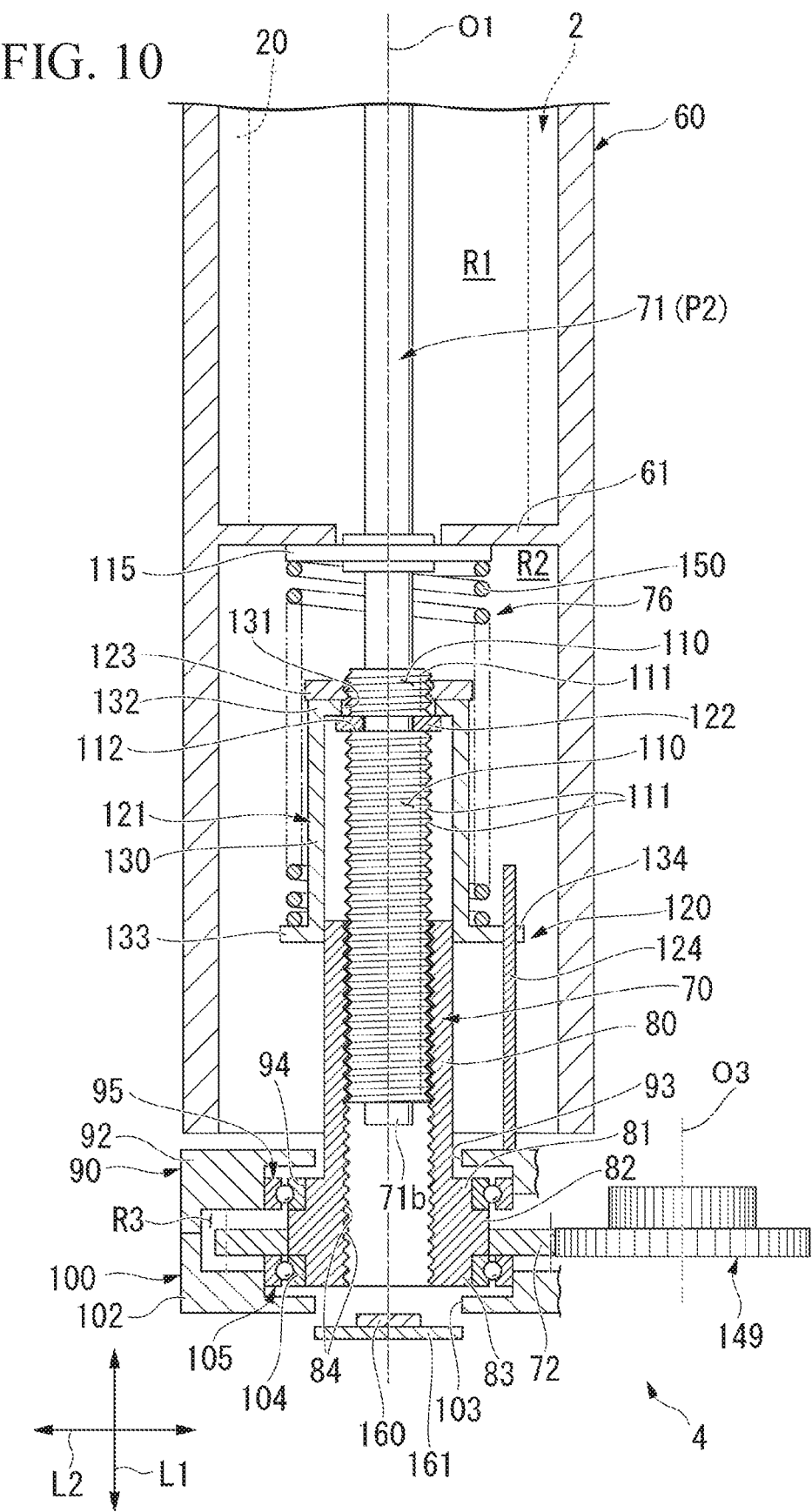
FIG. 10 is a longitudinal sectional view showing a state where the plunger screw moves upward to an end position from the state shown in FIG. 6.

The male screw portion 111 is screwed to the female screw portion 84 of the rotating cylinder 70 in a state where the rotation of the plunger screw 71 around the first axis O1 is restricted by the rotation restricting mechanism 120, and thus, the plunger screw 71 is not rotated by the rotation of the rotating cylinder 70. Accordingly, the plunger screw 71 can be linearly feed-moved upward from the start position P1 so that the distal end portion 71*a* of the plunger screw 71 is gradually separated from the rotating cylinder 70. As a result, finally, as shown in FIG. 10, it is possible to feed-move the plunger screw 71 to the end position P2.

Particularly, the plunger screw 71 is always biased toward the start position P1 side (downward) by the biasing mechanism 76 as indicated by an arrow F1 shown in FIG. 9. As a result, the male screw portion 111 is screwed into the female screw portion 84 on the rotating cylinder 70 side while being pressed to the start position P1 side. Therefore, the male screw portion 111 and the female screw portion 84 can be screwed together with little rattling, and occurrence of backlash in a fitting portion of the male screw portion 111 and the female screw portion 84 can be suppressed.

Accordingly, as shown by arrows F2 in FIG. 9, a rotational force of the rotating cylinder 70 can be efficiently transmitted to the plunger screw 71, and the plunger screw 71 can be stably and accurately moved up toward the end position P2 in response to the rotation of the rotating cylinder 70. Therefore, for example, the plunger screw 71 can be accurately feed-moved by a desired amount of movement from the start position P1 to the end position P2.

Thereby, as shown in FIG. 6, the reservoir plunger 22 can be pushed into the reservoir 2 via the distal end portion 71*a* of the plunger screw 71. Therefore, it is possible to extrude the medicinal solution W from the reservoir 2 by an amount of pushing the reservoir plunger 22 and dispense the medicinal solution W to the injection set 3 side. As a result, the medicinal solution W dispensed from the reservoir 2 can be guided to the injection patch 40 through the tube 42 and injected into the body of the user through the indwelling needle 43.

In particular, from the start position P1 to the end position P2, for example, the plunger screw 71 can be accurately feed-moved by a desired amount of movement, and thus, the medicinal solution W can be dispensed from the inside of the reservoir 2 by a desired amount. Therefore, for example, a predetermined amount of medicinal solution W can be dispensed from the inside of the reservoir 2 periodically with high accuracy and injected into the body of the user.

Furthermore, the power transmission mechanism 75 has the five two-stage gears 145 to 149. Accordingly, compared to a case where a plurality of spur gears are combined with each other in parallel in the related art, the driving force can be transmitted to the final gear 72 while saving space is realized. Therefore, the power transmission mechanism 75 can be designed compactly, and as a result, the entire feeding device 4 and liquid feeding device 5 can be reduced in size.

Further, unlike the related art, by rotating the rotating cylinder 70 in which the female screw portion 84 is formed, the plunger screw 71 in which the male screw portion 111 is formed and a decrease in the diameter is easily realized can be feed-moved. Accordingly, compared to the related art, it is possible to decrease a diameter size of the movable portion. Therefore, it is not necessary to secure a large movable space necessary for the movement of the plunger screw 71, and a dead space can be reduced correspondingly. Also in this respect, the entire feeding device 4 and liquid feeding device 5 can be reduced in size.

Moreover, the plunger screw 71 in which the decrease in the diameter is easily realized is feed-moved, and thus, it is possible to decrease the diameter of the rotating cylinder 70 itself which moves the plunger screw 71. Therefore, roundness of the rotating cylinder 70 is easily improved, and thus, the plunger screw 71 is easily held straightly along the first axis O1 with less inclination. Therefore, it is possible to stably feed-move the plunger screw 71 with excellent straightness.

As described above, according to the medicinal injection device 1 of the present embodiment, it is possible to stably and accurately feed-move the plunger screw 71, and thus, a predetermined amount of medicinal solution W can be accurately injected into the body of the user. Moreover, the entire feeding device 4 and liquid feeding device 5 can be reduced in size, it is easy to carry and can be reduced in weight, and thus, a burden on the user can be reduced.

According to the medicinal injection device 1 of the present embodiment, the stepping motor 74 and the power transmission mechanism 75 are disposed to be arranged in a row along the virtual axis O3. In addition, the stepping motor 74 and the power transmission mechanism 75 are disposed in parallel to the rotating cylinder 70 and the plunger screw 71, and thus, the stepping motor 74, the power transmission mechanism 75, the rotating cylinder 70, and the plunger screw 71 can be disposed in a compact manner in a collected state. Accordingly, the entire feeding device 4 and liquid feeding device 5 can be easily reduced in size, and in particular, it is possible to effectively suppress an increase in the upward-downward direction L1.

Moreover, it is possible to bias the plunger screw 71 by a simple method using only the elastic restoring force of the coil spring 150, and thus, a configuration can be easily simplified without adopting a complicated configuration. Moreover, the coil spring 150 is elastically deformed according to the feed-movement of the plunger screw 71, and thus, the elastic restoring force increases as the plunger screw 71 moves from the start position P1 to the end position P2. Therefore, the coil spring 150 can bias the plunger screw 71 strongly. Therefore, for example, even when fitting portions of the female screw portion 84 and the male screw portion 111 decrease according to the feed-movement of the plunger screw 71, the male screw portion 111 in a remaining fitting portion can be reliably pressed against the female screw portion 84 to the start position P1 side. Therefore, it is possible to effectively suppress occurrence of backlash.

Moreover, when the stepping motor 74 is driven by one step angle, the plunger screw 71 moves by a screw pitch of the male screw portion 111. Accordingly, an amount of feed-movement of the plunger screw 71 can be controlled using the number of drive pulses. Therefore, it is possible to accurately dispense a small amount of medicinal solution W from the reservoir 2 and inject the medicinal solution W into the body of the user. The amount of medicinal solution extruded from the reservoir 2 is determined by a cross-sectional area defined by the inner diameter of the reservoir barrel 20 and the amount of movement of the reservoir plunger 22, that is, the amount of movement of the plunger screw 71. Therefore, the smaller the amount of movement of the plunger screw 71, the amount of medicinal solution extruded from the reservoir 2 can be made very small. According to the present embodiment, the plunger screw 71 can be moved by the screw pitch of the male screw portion 111. Accordingly, for example, the minimum amount of medicinal solution extruded from the reservoir 2 can be suppressed to about 0.01 µl (microliter), and thus, it possible to accurately control the injection of the medicinal solution W.

Further, since the stepping motor 74 is used, the stepping motor 74 can be stably stopped by own holding force even in a state where the drive pulse is not input. Therefore, the driving gear 73 can be prevented from rotating unexpectedly, and as a result, the plunger screw 71 can be prevented from moving unexpectedly. Accordingly, for example, the medicinal solution W can be prevented from being injected into the body of the user at an unintended timing.

Meanwhile, as shown in FIG. 10, in a case where the plunger screw 71 reaches the end position P2, for example, the medicinal solution W in the reservoir 2 is completely dispensed. In this case, the control unit can detect that the plunger screw 71 reaches the end position P2 based on the rotating speed of the stepping motor 74 detected by the rotation sensor 170. Accordingly, the control unit performs a control so that the stepping motor 74 is rotated in the reverse direction and the plunger screw 71 is moved downward from the end position P2 toward the start position P1. Thereby, the plunger screw 71 can be returned to the start position P1 as shown in FIG. 6.

In addition, after the control unit returns the plunger screw 71 to the start position P1, for example, the control unit displays information that prompts exchange of the reservoir 2 on the display unit 51. Therefore, the user can perform an exchange operation for a new reservoir 2. In particular, if the plunger screw 71 returns to the start position P1, the proximal end portion 71*b* of the plunger screw 71 presses and displaces the contact-type displacement sensor 160. Thereby, the contact-type displacement sensor 160 outputs a detection signal to the control unit. Therefore, the control unit can accurately determine whether or not the plunger screw 71 is returned to the start position P1 based on the detection signal. Accordingly, for example, the exchange of the reservoir 2 or the like can be performed in a state where the plunger screw 71 is reliably located at the start position P1.

Hereinbefore, the embodiment of this invention is described. However, the embodiment is shown as an example and limits a scope of the invention. The embodiment can be implemented in various other forms, and various omissions, replacements, and modifications can be made within a scope which does not depart from the gist of the invention. For example, embodiments and modifications thereof include those which can be easily assumed by a person skilled in the art, substantially the same, and equivalents.

For example, in the above embodiment, the medicinal solution is extruded using the feeding device from the reservoir incorporated into the liquid feeding device, and the medicinal solution extruded using the injection set is injected into the body of the user. However, the present invention is not limited to this case. For example, a so-called patch type liquid feeding device may be configured in which the liquid feeding device itself can be attached to the body surface and which has the indwelling needle. In this case, for example, the medicinal solution extruded from the reservoir using a feeding device can be directly introduced into the indwelling needle without passing through the tube and can be injected into the body.

Further, the content is not limited to the medicinal solution, and may be other liquids or air such as gas. The content may be appropriately changed according to intended use and purpose. Furthermore, the plunger screw feed-moved by the feeding device may be used for purposes other than the liquid feeding.

Moreover, in the embodiment, the configuration is described in which the power transmission mechanism includes the five two-stage gears as the intermediate gears. However, the number of intermediate gears is not limited to five as long as at least one intermediate gear is the two-stage gear. For example, one two-stage gear and two spur gears may be provided as the intermediate gear, and the power transmission mechanism may be configured by combining the gears. Even in this case, a size can be reduced as compared to a case where the spur gears are combined in the related art.

According to the present invention, it is possible to feed-move the movable shaft stably and accurately, and to reduce the size. Therefore, for example, in a case where the liquid feeding or the like is performed using the movable shaft, it is possible to accurately feed a minute amount of liquid, and thus, the present invention can be appropriately used for a device that performs the liquid feeding. Accordingly, the present invention has industrial applicability.

While preferred embodiments of the invention have been described and shown above, it should be understood that these are exemplary of the invention and are not to be considered as limiting. Additions, omissions, substitutions, and other modifications can be made without departing from the spirit or scope of the present invention. Accordingly, the invention is not to be considered as being limited by the foregoing description, and is only limited by the scope of the appended claims.

What is claimed is:

1. A feeding device, comprising:
   a tubular body which has an inner peripheral surface on which a female screw portion is formed and is rotatably disposed around an axis;
   a movable shaft which has an outer peripheral surface on which a male screw portion is formed, is disposed inside the tubular body in a state where the male screw portion and the female screw portion are screwed to each other, wherein rotations of the movable shaft around the axis are restricted, and wherein the movable shaft is movable along a direction of the axis between a start position and an end position according to a rotation of the tubular body;
   a final gear which is provided on the tubular body;
   a drive unit comprising a driving gear;
   a power transmission mechanism comprising a plurality of intermediate gears and configured to transmit a driving force from the driving gear to the final gear via the plurality of intermediate gears; and
   a bias mechanism which is configured to apply a biasing force to the movable shaft along the direction of the axis,
   wherein the movable shaft is configured to move such that a distal end portion of the movable shaft is separated from the tubular body according to a movement of the movable shaft from the start position to the end position,
   wherein at least one of the plurality of intermediate gears is a two-stage gear having two gears whose diameters are different from each other, and
   wherein the bias mechanism is configured to apply the biasing force to the movable shaft from the end position toward the start position, and presses the male screw portion against the female screw portion to a start position side.

2. The feeding device according to claim 1,
   wherein the drive unit and the power transmission mechanism are disposed to be arranged in a row along a virtual axis parallel to the axis, and are disposed in parallel to the tubular body and the movable shaft.

3. The feeding device according to claim 1,
   wherein the bias mechanism includes a coil spring which is elastically deformable in the direction of the axis according to the movement of the movable shaft and biases the movable shaft toward the start position side by an elastic restoring force.

4. The feeding device according to claim 3,
   wherein the drive unit is a stepping motor, and
   wherein a gear ratio between the driving gear and the final gear is adjusted by the plurality of intermediate gears such that the movable shaft moves by a screw pitch of the male screw portion when the stepping motor is driven by one step angle.

5. The feeding device according to claim 4,
   wherein the stepping motor has a torque characteristic in which a maximum rotational torque thereof is larger than a maximum elastic restoring force of the coil spring and a minimum rotational torque thereof is larger than a minimum elastic restoring force of the coil spring.

6. The feeding device according to claim 1,
   wherein the movable shaft has a proximal end portion which is disposed to penetrate the tubular body and is disposed in a state of being exposed to an outside of the tubular body at the start position, and
   wherein the feeding device further comprises a detection sensor configured to detect the proximal end portion when the movable shaft is located at the start position and which is disposed outside the proximal end portion of the movable shaft in the direction of the axis.

7. The feeding device according to claim 2,
   wherein the bias mechanism includes a coil spring which is elastically deformable in the direction of the axis according to the movement of the movable shaft and biases the movable shaft toward the start position side by an elastic restoring force.

8. The feeding device according to claim 7,
   wherein the drive unit is a stepping motor, and
   wherein a gear ratio between the driving gear and the final gear is adjusted by the plurality of intermediate gears such that the movable shaft moves by a screw pitch of the male screw portion when the stepping motor is driven by one step angle.

9. The feeding device according to claim 8,
   wherein the stepping motor has a torque characteristic in which a maximum rotational torque thereof is larger than a maximum elastic restoring force of the coil spring and a minimum rotational torque thereof is larger than a minimum elastic restoring force of the coil spring.

10. A portable dispensing device comprising:

the feeding device according to claim 1; and a portable main body case which accommodates the feeding device, wherein the main body case includes an accommodation case, the accommodation case accommodating a reservoir, which includes a reservoir barrel filled with a content and a reservoir plunger disposed to be slidable in the reservoir barrel and in which the content is extruded according to a movement of the reservoir plunger, in a state where the reservoir is coaxially disposed with the axis, and wherein the distal end portion of the movable shaft is in contact with the reservoir plunger at the start position in a state where pushing is allowed.

\* \* \* \* \*

UNITED STATES PATENT AND TRADEMARK OFFICE
CERTIFICATE OF CORRECTION

| | |
|---|---|
| PATENT NO. | : 11,446,433 B2 |
| APPLICATION NO. | : 16/703363 |
| DATED | : September 20, 2022 |
| INVENTOR(S) | : Endo et al. |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 305 days.

Signed and Sealed this
Tenth Day of September, 2024

Katherine Kelly Vidal
*Director of the United States Patent and Trademark Office*